United States Patent
Boyd et al.

(10) Patent No.: US 9,931,292 B2
(45) Date of Patent: *Apr. 3, 2018

(54) ORAL CARE WHITENING COMPOSITIONS

(75) Inventors: Thomas Boyd, Metuchen, NJ (US); Dennis Ontumi, Easton, PA (US); Prakasarao Mandadi, Flemington, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 155 days.

This patent is subject to a terminal disclaimer.

(21) Appl. No.: 14/366,340

(22) PCT Filed: Dec. 20, 2011

(86) PCT No.: PCT/US2011/066087
§ 371 (c)(1),
(2), (4) Date: Jun. 18, 2014

(87) PCT Pub. No.: WO2013/095369
PCT Pub. Date: Jun. 27, 2013

(65) Prior Publication Data
US 2015/0037266 A1  Feb. 5, 2015

(51) Int. Cl.
*A61K 8/89* (2006.01)
*A61K 8/81* (2006.01)
*A61Q 11/00* (2006.01)
*A61C 19/06* (2006.01)
*A61K 8/891* (2006.01)
*A61K 8/892* (2006.01)
*A61K 8/22* (2006.01)
*A61K 8/04* (2006.01)
*A61K 8/49* (2006.01)
*A61K 8/92* (2006.01)

(52) U.S. Cl.
CPC .......... *A61K 8/8176* (2013.01); *A61C 19/066* (2013.01); *A61K 8/042* (2013.01); *A61K 8/22* (2013.01); *A61K 8/49* (2013.01); *A61K 8/89* (2013.01); *A61K 8/891* (2013.01); *A61K 8/892* (2013.01); *A61K 8/92* (2013.01); *A61Q 11/00* (2013.01); *A61K 2800/31* (2013.01); *A61K 2800/40* (2013.01); *A61K 2800/48* (2013.01); *A61K 2800/54* (2013.01); *A61K 2800/872* (2013.01)

(58) Field of Classification Search
USPC ........................................... 424/53
See application file for complete search history.

(56) References Cited

U.S. PATENT DOCUMENTS

| 3,733,403 | A | 5/1973 | Chen |
|---|---|---|---|
| 6,613,812 | B2 | 9/2003 | Bui et al. |
| 7,135,167 | B2 | 11/2006 | Legrand et al. |
| 8,540,971 | B2 | 9/2013 | Zaidel et al. |
| 9,517,194 | B2 | 12/2016 | Zaidel et al. |
| 2003/0211055 | A1* | 11/2003 | Montgomery ........... A61K 8/11 424/50 |
| 2005/0038181 | A1 | 2/2005 | Chopra et al. |
| 2005/0063923 | A1 | 3/2005 | Prencipe et al. |
| 2005/0069502 | A1 | 3/2005 | Chopra et al. |
| 2005/0137109 | A1 | 6/2005 | Quan et al. |
| 2005/0287084 | A1 | 12/2005 | Ibrahim et al. |
| 2006/0045854 | A1 | 3/2006 | Zaidel et al. |
| 2006/0147394 | A1 | 7/2006 | Shastry et al. |
| 2007/0003494 | A1 | 1/2007 | Mori et al. |
| 2007/0253916 | A1 | 11/2007 | Maitra et al. |
| 2007/0264315 | A1 | 11/2007 | Fournie et al. |
| 2012/0328535 | A1 | 12/2012 | Zaidel et al. |

FOREIGN PATENT DOCUMENTS

| CN | 101005879 | 7/2007 |
|---|---|---|
| CN | 101272824 | 9/2008 |
| CN | 102188335 | 9/2011 |
| TW | 201143800 | 12/2011 |
| TW | 201338792 | 10/2013 |
| WO | WO 2005/018593 | 3/2005 |
| WO | WO 2006/026424 | 3/2006 |
| WO | 2006/083525 | 8/2006 |
| WO | WO 2007/083253 | 7/2007 |

OTHER PUBLICATIONS

International Search Report and the Written Opinion issued in International Application PCT/US2011/066087 mailed Nov. 14, 2012.
Colas, 2005, "Silicones in Pharmaceutical Applications," Dow Corning Healthcare Industries; 24 pages, published online.
Thomas, 2005, "Silicone Adhesives in Healthcare Applications," Dow Corning; www.dowcorning.com/publishedlit/52-1057-1.pdf, published online Jan. 16, 2005.

* cited by examiner

*Primary Examiner* — Walter Webb

(57) ABSTRACT

Described herein are whitening compositions comprised of a peroxide component, and an adhesion system, which effectively provide whitening using a remarkably low level of peroxide. Methods of making and using these compositions are also described herein.

16 Claims, No Drawings

ORAL CARE WHITENING COMPOSITIONS

BACKGROUND

Products that are presently available to whiten teeth include a variety of different ingredients, but the primary active ingredient is a peroxide source. These products typically contain substantial amounts of whitening agents, for example, greater than 5% of a peroxide source. However, in some countries, such as many European countries, regulatory authorities have prohibited such levels of peroxide in dental whitening products. Thus, products providing effective levels of whitening with lower amounts of peroxide are highly desirable.

SUMMARY

In some embodiments, the present invention provides a non-aqueous dental whitening composition comprising: a peroxide component comprising a peroxide source in the amount of about 0.1% to about 5% of the total weight of the composition; and an adhesion system comprising a hydrophobic component comprising a silicone adhesive and a dental surface adhesion enhancing agent; wherein the composition when applied to the teeth is sufficiently viscous to form an adherent, continuous layer of the composition on dental enamel surfaces and deliver an effective amount of the peroxide source to a tooth surface.

In some embodiments, the present invention provides methods of whitening a tooth comprising applying any of the compositions described herein to a tooth of a mammal.

Further areas of applicability of the present invention will become apparent from the detailed description and examples provided hereinafter. It should be understood that the detailed description and specific examples, while providing specific embodiments of the invention, are intended for illustration only and should in no way limit the scope of the invention.

DETAILED DESCRIPTION

In some embodiments, the composition of the present invention is a viscous liquid, preferably a gel, which maintains its consistency during storage enabling the product to be painted on the tooth surface with a soft applicator pen or brush.

In some embodiments, the composition of the present invention provides a stable vehicle that prevents the decomposition of the peroxide whitening agent during storage and before use.

Once applied on a tooth surface, the saliva on the tooth enamel surface to which the composition is applied will either dissolve or disintegrate the peroxide containing matrix resulting in a rapid decomposition of the peroxide, and thereby provide an effective concentration of the peroxide source at the tooth surface, despite its relatively low concentration in the composition. Surprisingly, this low concentration is capable of delivering an acceptable level of tooth whitening.

The whitening composition of the present invention is a portable viscous liquid or gel tooth whitener that can be applied to the teeth as a coated layer conveniently painted onto the tooth enamel surface. Upon application to the teeth, the applied whitening composition forms an adherent layer of peroxide containing product that has the capacity to release the peroxide whitening agent over an extended period of time, e.g., from about 5 minutes to about 12 hours. The applied layer adheres to the tooth surface whereby the released peroxide source then whitens the teeth to which the composition is applied.

In some embodiments, the tooth whitening compositions of the present invention are substantially anhydrous, that is, no water is added. The composition may contain trace levels of water from ingredients or from product manufacture; however, such trace levels are insubstantial and do not interfere with the hydrophobic character of the composition.

The viscosity of a composition of the invention is greater than about 1,000 centipoise (cPs) and less than about 900,000 cPs, in a more specific embodiment greater than about 10,000 cP and less than about 100,000 cPs, in a more specific embodiment greater than 50,000 cPs and less than 900,000 cPs, and in an even more specific embodiment from between about 200,000 cPs to about 600,000 cPs.

In some embodiments, the present invention comprises a hydrophobic component, carrier or base material that comprises a silicone polymer. The term "hydrophobic" or "water-insoluble" as applied to polymers and as employed herein refers to an organic polymer which is substantially non-aqueous having a water solubility of less than one gram per 100 grams of water at 25° C. Any such silicone polymers that are compatible with the whitening agents described herein, and which can produce a tooth whitening composition having a desired viscosity can be used.

In some embodiments, the hydrophobic polymers suitable for use in the present invention are referred to as "siloxane" polymers, which are also generally known in the art as "silicone" polymers. In certain embodiments of the present invention, the hydrophobic polymers that comprise the hydrophobic material are those in which a whitening agent can be dispersed and are well known in the art. Many such silicone polymers are commercially available. In various embodiments, a preferred silicone-based hydrophobic polymer is a polyorganosiloxane, in particular polydimethylsiloxane.

In some embodiments, the siloxane polymers that can function as part of the hydrophobic component are in the form of a fluid. Polysiloxane fluids useful herein for the hydrophobic silicone material component include those with a viscosity, at 25° C., of about 1 milliPascal-sec (mPa-s) to about 1000 mPa-s, or about 2 mPa-s to about 500 mPa-s, or about 20 mPa-s to about 400 mPa-s. Polysiloxane fluids for use herein can be linear or cyclic, and can be substituted with a wide variety of substituents. In certain embodiments, substituents include methyl, ethyl and phenyl substituents. Suitable polysiloxane fluids include linear polysiloxane polymers such as dimethicone and other low viscosity analogues of the polysiloxane materials, in certain embodiments having a viscosity, at 25° C., of 200 mPa-s or less and cyclomethicone, and other cyclic siloxanes having for example a viscosity, at 25° C., of 200 mPa-s or less. Other fluids include polysiloxane polyether copolymers and hydroxy terminated polydimethyl-siloxane fluid (e.g., Dow Corning ST-DIMETHICONOL™ 40, Dow Corning SGM 36, SGM3). Commercial examples of materials that are suitable for use herein include DC200 series fluids marketed by Dow-Corning Corporation and the AK Fluid series marketed by Wacker-Chemie GmbH, Munchen, Germany. High molecular silicone resins with a polysiloxane blend may also be used including powdered trimethylsiloxysilicate, for example, Dow Corning 593 fluid, Wacker Belsil TMS 803. Another suitable silicone fluid from Dow Corning is Q7-9210.

In some embodiments, at least part of the hydrophobic component is a silicone pressure sensitive adhesive (PSA).

Such PSAs can be produced by condensing a silicone resin and an organosiloxane such as a polydiorganosiloxane. Such hydrophobic polymers are an elastomeric, tacky material, adhesion of which to dental enamel surfaces can be varied by altering the ratio of silicone resin to polydiorganosiloxane in the copolymer molecule. Such polymers are pressure sensitive hydrophobic polymers specifically designed for pharmaceutical use and are permeable to many drug compounds and find application for the transdermal application of various compounds. In some embodiments, the silicone polymers are the copolymer product of mixing a silanol terminated polydiorganosiloxane such as polydimethyl siloxane with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. A catalyst, for example, an alkaline material, such as ammonia, ammonium hydroxide or ammonium carbonate, can be mixed with the silanol-terminated polydiorganosiloxane and the silicone resin to promote this crosslinking reaction. By copolymerizing the silicone resin with the silanol terminated polydiorganosiloxane, there results a polymer with self-adhering properties and the cohesive properties of a soft elastomer matrix characteristic of pressure sensitive polymers being distinguished from the hard, non-elastomeric properties of other silicone resins. In one embodiment, hydrophobic polymers used in the carrier are available from the Dow-Corning Company under the brand name BIO-PSA. The modification of a ratio of silicone resin to polydiorganosiloxane modifies the tackiness of the polymer. This ratio can be in the range of about 70:30 to about 50:50. For example, the BIO PSA silicone sold by Dow-Corning is available in three silicone resin to silicone polymer ratios namely, 65/35 (low tack), 60/40 (medium tack), 55/45 (high tack). Such a polyorganosiloxane PSA is available dissolved in either ethyl acetate solvent or dimethicone. Modifying the silicone resin to polydiorganosiloxane ratio of the PSA will modify the tackiness of the PSA. For example, the BIO PSA silicone adhesive sold by Dow-Corning is available in three silicone resin to silicone polymer ratios namely, 65/35 (low tack), 60/40 (medium tack), 55/45 (high tack) dissolved in either ethyl acetate solvent or dimethicone. A suitable silicone PSA is Silicone Adhesive 8-7016, commercially available from Dow Corning.

In some embodiments the hydrophobic component is present at a concentration of from about 20 to about 80%, by weight of the composition. In some embodiments, the hydrophobic component is present at a concentration of from about 40 to about 80%, by weight of the composition. In some embodiments, the hydrophobic component is present at a concentration of from about 60 to about 80%, by weight of the composition. In some embodiments, the hydrophobic component is present at a concentration of from about 70 to about 80%, by weight of the composition. In some embodiments, the hydrophobic component is present at a concentration of about 75%, by weight of the composition.

In some embodiments, adhesiveness is be measured using standard adhesion tests known in the art, for example, the adhesive test disclosed in U.S. Pat. No. 6,613,812 to Bui. In certain embodiments, the adhesiveness between a tooth and a film formed from a composition of the present invention can be from about at least 500 pounds per square inch (PSI), at least 1,000 PSI, at least 2,000 PSI, or greater.

The present inventors have discovered that particular amounts of a dental surface adhesion enhancing agent not only provides greater retention of the composition to the tooth surface, but also enhances the stability of the peroxide source and helps to maximize delivery of an effective concentration of the peroxide source at the target site.

In some embodiments, the compositions of the present invention optionally comprise a tartar control or anticalculus agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate (SHMP) and mixtures thereof. In a particular embodiment SHMP is used. The amount of stain prevention agent optionally present is from about 0.1% to about 10%, in another embodiment from about 2% to about 9%, and in another embodiment from about 5% to about 8%, or about 7%, by weight, of the composition.

In some embodiments, the compositions of the present invention comprise a flavoring agent. Suitable flavoring agents include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is incorporated in the whitening liquid composition of the present invention at a concentration of about 0.01 to about 2% by weight and preferably about 0.1 to about 0.5% by weight.

In some embodiments, the present invention provides a non-aqueous whitening composition comprising: a peroxide component comprising a peroxide source in the amount of about 0.1% to about 5% of the total weight of the composition; and an adhesion system comprising: a hydrophobic component comprising a silicone adhesive; and a dental surface adhesion enhancing agent, wherein the composition when applied to the teeth is sufficiently viscous to form an adherent, continuous layer on a dental surface and deliver an effective amount of said peroxide source to a tooth surface.

In some embodiments, the peroxide source is selected from: hydrogen peroxide; urea peroxide, sodium percarbonate, sodium perborate; and a combination of two or more thereof.

In some embodiments, the peroxide component further comprises cross-linked polyvinylpyrrolidone. In some embodiments, the peroxide source is complexed with the cross-linked polyvinyl pyrrolidone. In some embodiments, the peroxide source is hydrogen peroxide.

In some embodiments, the dental surface adhesion enhancing agent comprises an additional amount of cross-linked polyvinylpyrrolidone. In some embodiments, the additional amount of cross-linked polyvinylpyrrolidone is not complexed with the peroxide source.

In some embodiments, the peroxide source is present in an amount from about 0.05% to about 0.15%, by weight of the composition. In other embodiments, the peroxide source is present in an amount from about 0.08% to about 0.12%, by weight of the composition. In further embodiments, the peroxide source is present in the amount of about 0.1%, by weight of the composition.

In some embodiments, wherein the silicone adhesive is a pressure sensitive silicone adhesive. In some embodiments, the pressure sensitive silicone adhesive is a copolymer prepared by condensing a silicone resin with a polydiorganosiloxane. In some embodiments, the polydiorganosiloxane is polydimethylsiloxane. In some embodiments, the silicone resin is a silanol-containing silicone resin.

In some embodiments, the hydrophobic component further comprises a silicone fluid. In some embodiments, the silicone fluid comprises a siloxane polymer.

In some embodiments, the adhesion system further comprises a material selected from: bees wax, mineral oil, a blend of mineral oil and polyethylene (e.g., a plastigel), petrolatum, white petrolatum, a blend of liquid paraffin and a butene/ethylene/styrene hydrogenated copolymer (e.g., a versagel), a polyethylene wax, polyisobutene, a polyvinyl pyrrolidone/vinyl acetate copolymer; and a combination of two or more thereof. In some embodiments, the organic material comprises mineral oil.

In some embodiments, the dental surface adhesion enhancing agent is present in an amount of about 15% to about 25%, by weight, of the composition. In some embodiments, the dental surface adhesion enhancing agent is present in the amount of about 16% to about 20%, by weight, of the composition. In other embodiments, the dental surface adhesion enhancing agent is present at a concentration of about 18%, by weight, of the composition.

Further embodiments provide a method for whitening a tooth comprising applying a composition according to any one of the foregoing claims to a tooth of a mammal. In some embodiments, the composition is applied using a pen. In some embodiments, the composition is maintained on the surface of the tooth for a plurality of minutes.

In some embodiments, the composition is maintained on the surface of a tooth for from about 1 minute to about 8 hours. In some embodiments, the composition is maintained on the surface of a tooth for from about 5 minutes to about 4 hours. In some embodiments, the composition is maintained on the surface of a tooth for from about 10 minutes to about 120 minutes. In some embodiments, the composition is maintained on the surface of a tooth for from about 15 minutes to about 60 minutes. In some embodiments, the composition is maintained on the surface of a tooth for from about 20 minutes to about 45 minutes. In some embodiments, the composition is maintained on the surface of a tooth for about 30 minutes.

In some embodiments, the composition is in the form of a gel.

In some embodiments, the compositions of the present invention can be prepared by adding and mixing the ingredients of the composition in a suitable vessel such as a stainless steel tank provided with a mixer. In the preparation of the whitening compositions described herein, the ingredients are advantageously added to the mixer in the following order: hydrophobic component, peroxide component, dental surface adhesion enhancing agent, and any desired flavoring or sweetener. The ingredients are then mixed to form a homogeneous dispersion/solution.

In some embodiments, the compositions of the present invention are applied to the tooth of a subject, by manual application, such as by painting the teeth with a soft applicator brush in the same manner as application of nail polish to a finger nail and without the intervention of a dentist or technological operations. Application by the user, leaves a coating of the thick liquid suspension on the teeth. Contact with saliva causes the slow release of $H_2O_2$ from the matrix of the peroxide component, and permits efficient delivery of the peroxide source to the target site, e.g. the tooth.

Typically, the compositions are applied directly to the teeth, e.g., by painting the teeth for a time sufficient to effect whitening. The compositions of the present invention can be used in a regimen for whitening teeth and can be used in combination with a whitening toothpaste and a whitening mouthwash to further enhance the whitening results.

As used herein, "whitening" refers to a change in visual appearance of a tooth, preferably such that the tooth has a brighter shade. Increase in whiteness of a dental surface can be observed visually, for example with the aid of color comparison charts or gauges, or measured by colorimetry, using any suitable instrument such as a Minolta Chromameter, e.g., model CR-400 (Minolta Corp., Ramsey, N.J.). The instrument can be programmed, for example, to measure Hunter Lab values or L*a*b* values according to the standard established by the International Committee of Illumination (CIE). The L*a*b* system provides a numerical representation of three-dimensional color space where L* represents a lightness axis, a* represents a red-green axis and b* represents a yellow-blue axis. The L* and b* axes are typically of greatest applicability to measurement of tooth whiteness. Increase in whiteness can be computed from differences in L*, a* and b* values before and after treatment, or between untreated and treated surfaces.

As used herein, "tooth" or "teeth" refers to natural mammalian teeth, dentures, dental plates, fillings, caps, crowns, bridges, dental implants, and the like, and any other hard surfaced dental prosthesis either permanently or temporarily fixed within the oral cavity.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1

Table 1 (below) provides the formulation for an exemplary composition of the present invention.

TABLE 1

Formula I

| Ingredient | Weight % |
| --- | --- |
| Silicone adhesive | 30 |
| Silicone fluid | 15.55 |
| PVP-$H_2O_2$ complex | 0.55% (0.1% $H_2O_2$) |
| Gelled mineral oil | 35 |
| cPVP | 18 |
| Sodium saccharin | 0.3 |
| Flavor | 0.6 |

Example 2

An exemplary composition (Formula I) of the present invention is compared to a similarly formulated composition (Comparative Example I) which contains more than forty times the amount of a peroxide source contained in Formula I.

Table 2 (below) provides the formulation for Comparative Example I.

TABLE 2

Comparative Example I

| Ingredient | Weight % |
| --- | --- |
| Silicone adhesive | 30 |
| Silicone fluid | 14 |
| PVP-$H_2O_2$ complex | 25% (4.5% $H_2O_2$) |
| Gelled mineral oil | 30.1 |
| Sodium saccharin | 0.3 |
| Flavor | 0.6 |

Whitening efficacy is determined using a duplicate pair of flow cells designed to accommodate a total of eight bovine enamel blocks (four in each cell). Bovine enamel blocks are obtained freshly stained using an established staining protocol (Indiana University, Indianapolis, Ind.). The initial L*, a* and b* values are matched as closely as possible prior to the experiment using a chromameter (Minolta CR-321) based on initial L*, a* and b* values (CIELAB). The L, a, b values are measured four times at slightly differing locations on the surface of the bovine enamel blocks.

To simulate the saliva of the human mouth, an artificial saliva buffer solution maintained at 37° C. is prepared containing the salts usually present in saliva at levels typical to the levels found in human saliva.

The bovine enamel blocks are placed in the flow cells and the liquid compositions are evenly applied using a brush. Flow over the teeth was 0.6 ml/min. for 30 min. Average initial and final chromometer readings are read, and used to calculate Δb and ΔL.

TABLE 3

| | Δb* | ΔL |
| --- | --- | --- |
| Formula I | −3.36 | 4.38 |
| Comparative Example I | −4.12 | 8.3 |

The data described in Table 3 (above) demonstrates that compositions of the present invention unexpectedly provide a level of whitening comparable to a similarly formulated composition containing over 40× more whitening agent.

The invention claimed is:

1. A non-aqueous oral care composition comprising:
   a peroxide component comprising a peroxide source in the amount of 0.05% to 0.15% of the total weight of the composition; and
   40% to 80% of an adhesion system comprising:
   a hydrophobic component comprising a silicone adhesive, a silicone fluid and a dental surface adhesion enhancing agent comprising crosslinked polyvinylpyrrolidone that is not complexed with a peroxide source;
   wherein the composition when applied to the teeth is sufficiently viscous to form an adherent, continuous layer on a dental surface and deliver an effective amount of said peroxide source to a tooth surface
   wherein the composition is substantially anhydrous.

2. The composition of claim 1 wherein the peroxide source is selected from the group consisting of hydrogen peroxide; urea peroxide, sodium percarbonate, sodium perborate; and a combination of two or more thereof.

3. The composition of claim 1, wherein the peroxide component further comprises cross-linked polyvinylpyrrolidone, wherein the peroxide source is complexed with the cross-linked polyvinyl pyrrolidone.

4. The composition of claim 1 wherein the peroxide source is hydrogen peroxide.

5. The composition of claim 1 wherein the peroxide source is present in an amount from about 0.08% to about 0.12%, by weight of the composition.

6. The composition of claim 1, wherein the peroxide source is present in the amount of about 0.1%, by weight of the composition.

7. The composition of claim 1, wherein the silicone adhesive is a pressure sensitive silicone adhesive.

8. The composition of claim 7, wherein the pressure sensitive silicone adhesive is a copolymer prepared by condensing a silicone resin with a dihydroxy polydiorganosiloxane.

9. The composition of claim 8, wherein the dihydroxy polydiorganosiloxane is dihydroxy polydimethylsiloxane.

10. The composition of claim 1, wherein the silicone resin is a silanol-containing silicone resin.

11. The composition of claim 1, wherein the dental surface adhesion enhancing agent is present in an amount of about 15% to about 25%, by weight, of the composition.

12. The composition of claim 1, wherein the dental surface adhesion enhancing agent is present in the amount of about 16% to about 20%, by weight, of the composition.

13. The composition of claim 1, wherein the dental surface adhesion enhancing agent is present at a concentration of about 18%, by weight, of the composition.

14. A method for whitening a tooth comprising applying a composition of claim 1 to a tooth of a mammal.

15. The method of claim 14, wherein the composition is applied using a pen.

16. The method of claim 14, wherein the composition is maintained on the surface of the tooth for a plurality of minutes.

* * * * *